United States Patent
Skaling

(10) Patent No.: US 8,525,527 B2
(45) Date of Patent: Sep. 3, 2013

(54) HELICAL SENSOR FOR TESTING A COMPOSITE MEDIUM

(75) Inventor: Whitney Skaling, Buellton, CA (US)

(73) Assignee: Soilmoisture Equipment Corporation, Goleta, CA (US)

(*) Notice: Subject to any disclaimer, the term of this patent is extended or adjusted under 35 U.S.C. 154(b) by 260 days.

(21) Appl. No.: 12/627,788

(22) Filed: Nov. 30, 2009

(65) Prior Publication Data

US 2011/0128026 A1    Jun. 2, 2011

(51) Int. Cl.
*G01R 27/04* (2006.01)

(52) U.S. Cl.
USPC .......................... 324/643; 324/663; 324/642

(58) Field of Classification Search
USPC .................................................. 324/643, 640
See application file for complete search history.

(56) References Cited

U.S. PATENT DOCUMENTS

| | | | | |
|---|---|---|---|---|
| 3,038,848 A * | 6/1962 | Brewer et al. | | 204/409 |
| 3,240,693 A * | 3/1966 | Gardner | | 204/430 |
| 3,255,408 A | 6/1966 | Walker | | |
| 3,509,452 A * | 4/1970 | Walker | | 324/632 |
| 3,703,829 A | 11/1972 | Dougherty | | |
| 3,965,416 A | 6/1976 | Friedman | | |
| 4,954,238 A | 9/1990 | Kato et al. | | |
| 5,608,318 A * | 3/1997 | Yasui | | 324/233 |
| 5,818,241 A | 10/1998 | Kelly | | |
| 5,819,582 A | 10/1998 | Kelly | | |
| 6,018,247 A * | 1/2000 | Kelly | | 324/644 |
| 6,281,801 B1 | 8/2001 | Cherry et al. | | |
| 6,293,142 B1 * | 9/2001 | Pchelnikov et al. | | 73/290 R |
| 6,320,393 B1 * | 11/2001 | Yasui et al. | | 324/663 |
| 6,441,622 B1 * | 8/2002 | Wrzesinski et al. | | 324/643 |
| 6,675,645 B1 | 1/2004 | Pchelnikov | | |
| 6,697,675 B1 * | 2/2004 | Safarevich et al. | | 607/116 |
| 7,042,234 B2 | 5/2006 | Buss | | |
| 7,228,900 B2 * | 6/2007 | Schultz et al. | | 166/250.01 |

* cited by examiner

*Primary Examiner* — Richard Isla Rodas
(74) *Attorney, Agent, or Firm* — Lyon & Harr, LLP; Richard T. Lyon

(57) ABSTRACT

A sensor is provided for testing a composite medium. The sensor includes a tube and three or more conductors which are wound in a continuously parallel helix around the tube such that the conductors are interleaved. The tube is non-porous and electrically insulative. Both the proximal end and the distal end of the tube are open. Each turn of each conductor is equally spaced from the adjoining turns of the other conductors, and the conductors have a common helical length. The sensor can also include a first cap which seals the proximal end of the tube and a second cap which seals the distal end of the tube such that the interior of the tube is always filled with air.

23 Claims, 5 Drawing Sheets

HELICAL SENSOR FOR TESTING A COMPOSITE MEDIUM

BACKGROUND

A probe or sensor is commonly used to test a medium of interest. The probe/sensor is disposed in or around the medium being tested. The testing generally determines various properties of the medium and optionally monitors the medium on an ongoing basis to automatically detect changes in its properties. The design and configuration of the probe/sensor are typically adapted to the specific type of medium being tested and the specific type(s) of medium properties being determined.

SUMMARY

This Summary is provided to introduce a selection of concepts, in a simplified form, that are further described hereafter in the Detailed Description. This Summary is not intended to identify key features or essential features of the claimed subject matter, nor is it intended to be used as an aid in determining the scope of the claimed subject matter.

Helical sensor embodiments described herein generally involve a sensor for testing a composite medium. In one exemplary embodiment the sensor includes a tube and three or more conductors which are wound in a continuously parallel helix around the tube such that the conductors are interleaved. The tube is non-porous and electrically insulative. Both the proximal end and the distal end of the tube are open. Each turn of each conductor is equally spaced from the adjoining turns of the other conductors, and the conductors have a common helical length. In another exemplary embodiment the sensor also includes a first cap which seals the proximal end of the tube and a second cap which seals the distal end of the tube such that the interior of the tube is always filled with air. The first and second caps are also non-porous and electrically insulative.

In yet another exemplary embodiment an open sensor includes a longitudinal section of the tube, where an interior surface of the tube section forms a trough. One or more conductors, each having a dielectric coating applied to its upper surface, are successively layered on top of each other, where the bottommost conductor runs along the interior surface of the tube section. A topmost conductor is layered on top of the one or more conductors. Each conductor runs from a proximal end of the tube section to a distal end of the tube section in a repeating serpentine pattern. The conductors are longitudinally offset from each other such that the conductors are interleaved along the interior surface of the tube section. The conductors cross each other only at the longitudinal sides of the interior surface. The conductors are equally spaced from each other and have a common length.

DESCRIPTION OF THE DRAWINGS

The specific features, aspects, and advantages of the helical sensor embodiments described herein will become better understood with regard to the following description, appended claims, and accompanying drawings where:

DETAILED DESCRIPTION

In the following description of helical sensor embodiments reference is made to the accompanying drawings which form a part hereof, and in which are shown, by way of illustration, specific embodiments in which the helical sensor can be practiced. It is understood that other embodiments can be utilized and structural changes can be made without departing from the scope of the helical sensor embodiments.

1.0 Helical Sensor for Testing a Composite Medium

Generally speaking, the helical sensor embodiments described herein are applicable to testing a composite medium. The term "composite medium" is used herein to refer to a medium which is composed of two or more different substances, where the substances may include solids such as minerals and organic compositions, air and/or other gases, and one or more liquids, among other things. The testing can measure one or more dielectric influences in the medium and/or one or more characteristics of the medium. Exemplary dielectric influences in the medium which can be measured include the volumetric liquid content of the medium, the salinity (i.e., salt content) of the medium, and mixing ratios, among other things. Exemplary characteristics of the medium which can be measured include the temperature of the medium, and other detectable physical or chemical properties of the medium.

The helical sensor embodiments described herein are advantageous for a variety of reasons including, but not limited to, the following. Very precise measurements of the dielectric influences in the medium can be made even when the medium has a very small content of the dielectric influences. The measurements can be made and then analyzed very quickly, thus allowing a variety of different conductor pairs to be used in the analysis. The measurements can be made and analyzed either once at a particular point in time, or on an ongoing basis over a period of time using automation. Thus, the medium can be continually monitored and any changes in its properties can be automatically detected. By way of example but not limitation, changes in the physical state of the medium can be detected.

Furthermore, a wide variety of different types of composite media can be tested such as soil (which may include substances such as clay, sediments and organic matter), wood, rock, concrete, slurries of various sorts, foodstuffs, and grains, among other things. The media can be tested in situ (e.g., one or more sensors can be disposed at different locations in a farm field or the like), or a sample of the media can be taken (such as a core sample and the like) and subsequently tested in a different setting such as a laboratory environment or the like.

Additionally, a wide variety of different types of liquids having different dielectric natures can be measured such as water, oil, milk, glycol, and honey, among other things. The liquid being measured can also be any homogenized mixture of different substances in a liquid form.

1.1 System Environment

Figure 1:
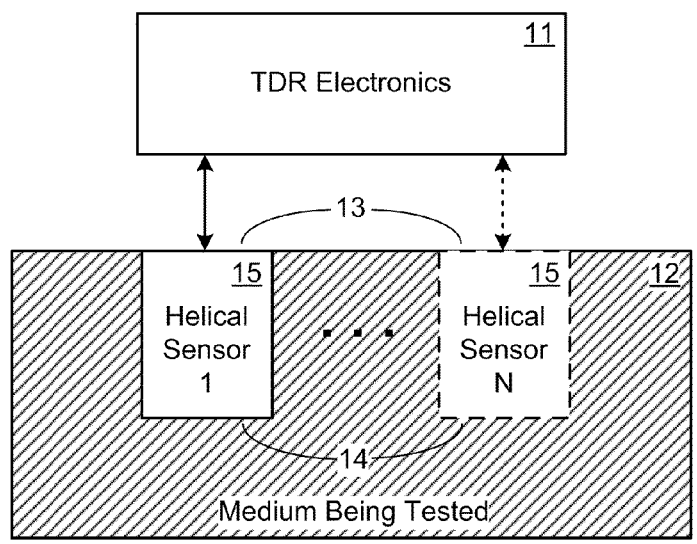
FIG. 1 is a diagram illustrating an exemplary embodiment, in simplified form, of a system for implementing the helical sensor embodiments described herein.

FIG. 1 illustrates an exemplary embodiment, in simplified form, of a suitable system environment in which the helical sensor embodiments described herein can be implemented. The environment illustrated in FIG. 1 is only one example of a suitable system environment and is not intended to suggest any limitation as to the scope of use or functionality of the helical sensor embodiments. Neither should the system environment be interpreted as having any dependency or requirement relating to any one or combination of the components discussed hereafter in this section.

As exemplified in FIG. 1, a suitable system environment for implementing the helical sensor embodiments described herein generally includes the following components. One or more helical sensors 15 are disposed within a composite medium which is being tested 12. In the situation where a plurality of sensors 15 are used, each sensor could be disposed at a different location within the medium 12 so as to provide an analysis of the medium which covers a larger vertical and/or horizontal area. Time-domain reflectometry (TDR) electronics 11 are electrically connected to the proximal end 13 of each of the sensors 15. The TDR electronics 11 interoperate with each sensor 15 individually to test the medium 12. Generally speaking, the TDR electronics 11 include a signal generator module (not shown), a signal detector module (not shown) and a signal processor module (not shown) whose operation will be described in more detail hereafter. In the situation where a plurality of sensors 15 are used, the TDR electronics 11 also include a signal multiplexer module (not shown) which generally allows the signal generator, signal detector and signal processor modules to be time-shared amongst each of the sensors.

Referring again to FIG. 1, the TDR electronics 11 interoperate with each helical sensor 15 individually in a time-shared manner as follows. Generally speaking and as will be described in more detail hereafter, the sensor 15 includes three or more helical conductors which form a plurality of transmission lines (also known as "wave guides") (not shown), where the transmission lines have a common length and each transmission line runs from the proximal end 13 of the sensor 15 to the distal end 14 of the sensor. The signal generator module transmits an original, short rise-time, short duration electrical pulse into the proximal end 13 of each transmission line and into the signal processor module, which records the original electrical pulse that is transmitted into each transmission line. Each transmission line provides a means for the original electrical pulse that is transmitted there-into and a resulting reflected electrical pulse to propagate along the sensor as follows.

Referring again to FIG. 1, the original electrical pulse which is transmitted into a given transmission line propagates along the transmission line from the proximal end 13 of the helical sensor 15 toward the distal end 14 of the sensor. When the original pulse reaches the end of the transmission line at the distal end 14 of the sensor 15, the original pulse is reflected, thus generating a reflected electrical pulse which propagates along the transmission line from the distal end of the sensor back toward the proximal end 13 of the sensor. When the reflected pulse reaches the proximal end 13 of the sensor 15, the reflected pulse is received by the signal detector module. The signal detector module then passes the reflected pulse it received from the transmission line to the signal processor module which records this received reflected pulse. Generally speaking and as will be described in more detail hereafter, the signal processor module can analyze the reflected pulse it receives from each transmission line and compare it to the original pulse that was transmitted into the transmission line in a variety of different ways in order to compute a current measurement of one or more dielectric influences in the medium 12, or a current measurement of one or more characteristics of the medium.

In one embodiment of the TDR electronics a common original electrical pulse can be transmitted into each transmission line at the same time. In another embodiment of the TDR electronics the common original electrical pulse can be transmitted into the different transmission lines at different times. In yet another embodiment of the TDR electronics different original electrical pulses can be transmitted into the different transmission lines, either at the same time or at different times.

1.2 Helical Sensor

Figure 3:
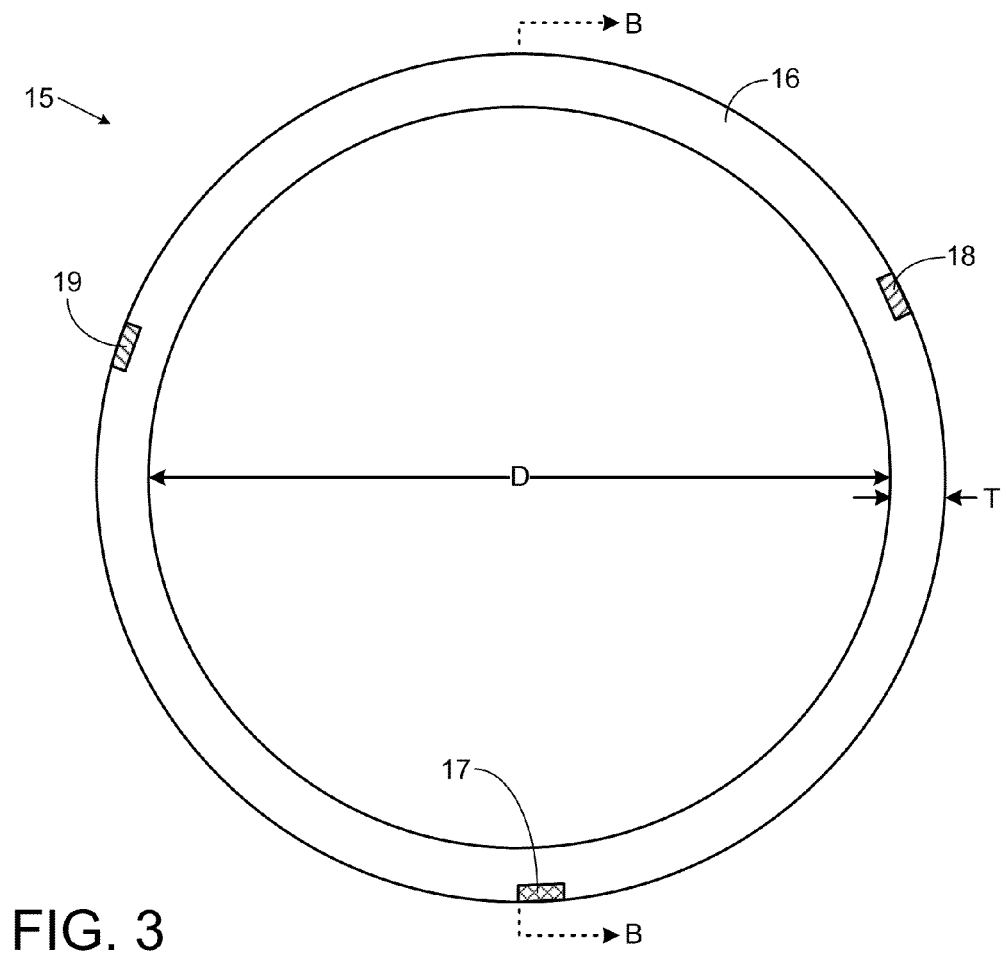
FIG. 3 is a diagram illustrating a top view, in simplified form, of the helical sensor of FIG. 2.
Figure 2:
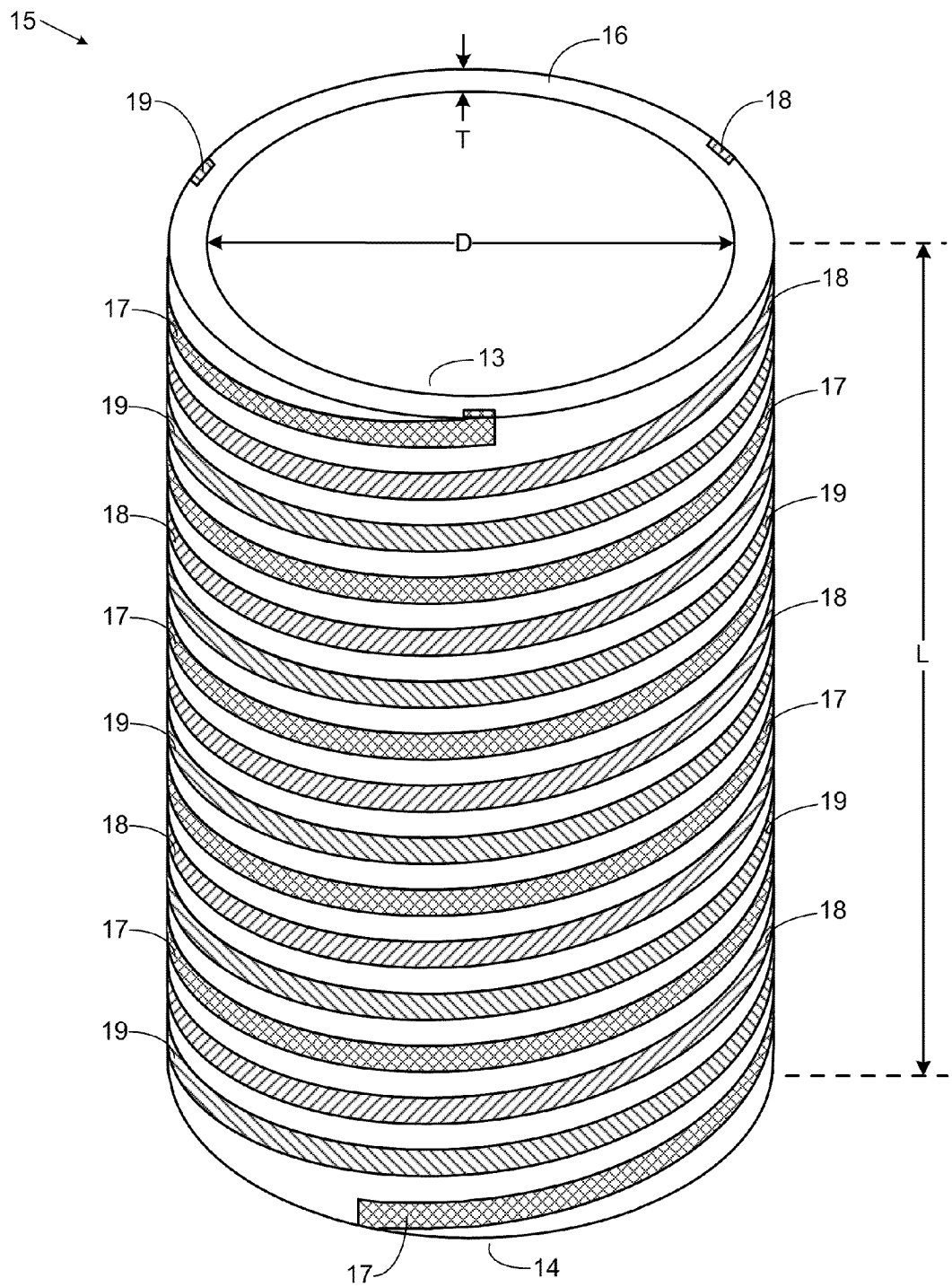
FIG. 2 is a diagram illustrating a longitudinal perspective view, in simplified form, of an exemplary embodiment of the helical sensor.
Figure 4:
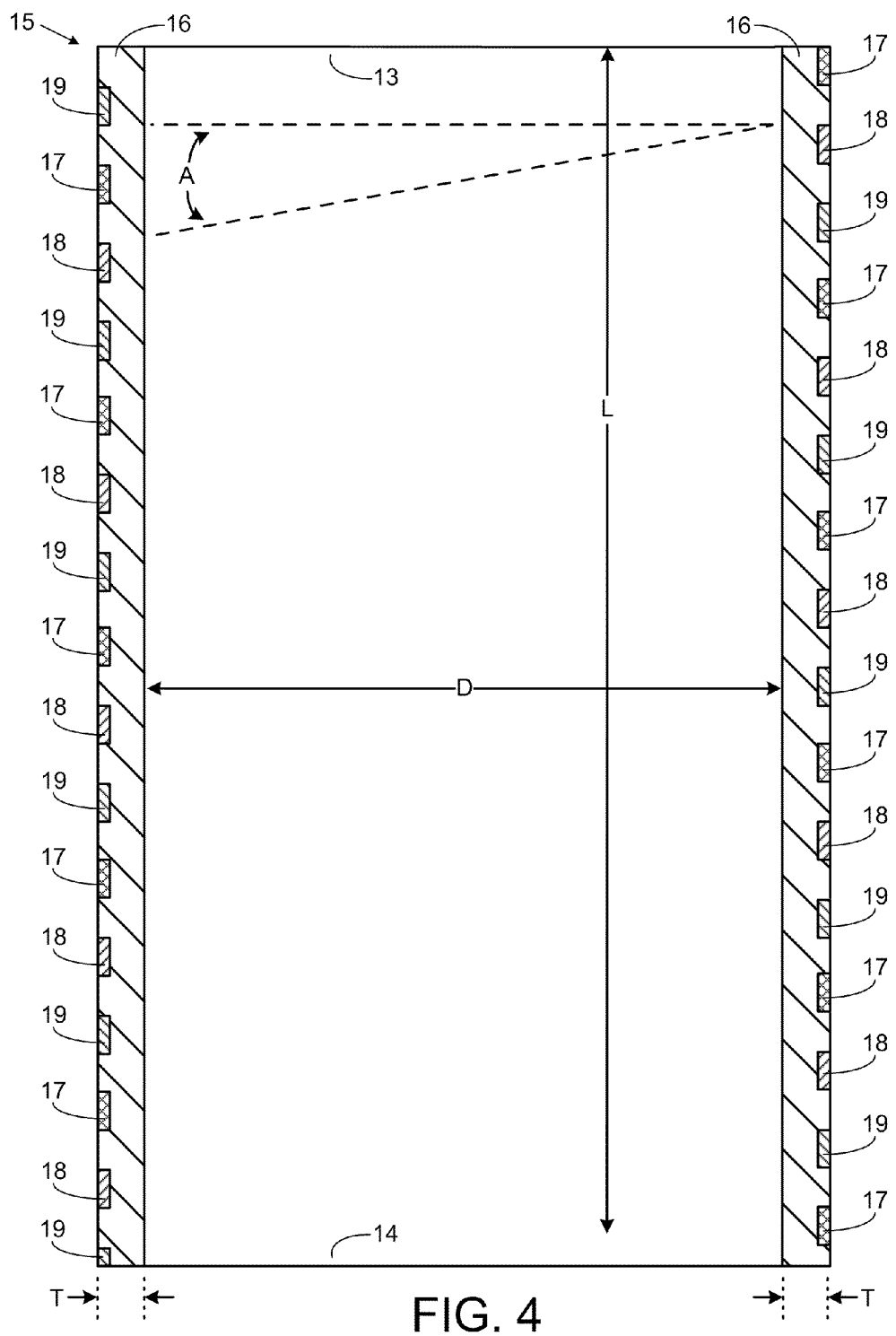
FIG. 4 is a diagram illustrating a longitudinal cross-sectional view, in simplified form, of the helical sensor of FIG. 2 taken along line B-B of FIG. 3.

FIGS. 2-4 illustrate an exemplary embodiment, in simplified form, of the aforementioned helical sensor. More particularly, FIG. 2 illustrates a longitudinal perspective view of an exemplary embodiment of the helical sensor. FIG. 3 illustrates a top view of the sensor of FIG. 2. FIG. 4 illustrates a longitudinal cross-sectional view of the sensor of FIG. 2 taken along line B-B of FIG. 3. Generally speaking and as exemplified in FIGS. 2-4, the sensor 15 includes a first helical conductor 17, a second helical conductor 18 and a third helical conductor 19 which are wound in a continuously parallel helix around a tube 16 using a prescribed winding angle A such that these conductors are interleaved. Each turn of each helical conductor is equally spaced from the adjoining turns of the other two helical conductors (e.g., each turn of the second helical conductor 18 is equally spaced from the adjoining turns of the first and third helical conductors 17 and 19). The helical conductors 17/18/19 have a common helical length (i.e., the total length of each helical conductor from the proximal end 13 of the tube to the distal end 14 of the tube is the same). The distal end of each helical conductor is unterminated.

Referring again to FIGS. 2-4, the tube 16 has a prescribed longitudinal length L, a prescribed interior diameter D and a prescribed wall thickness T. The proximal end 13 of the tube 16 and the distal end 14 of the tube are open. The helical sensor 15 can be used to test a sample of a composite medium 12 by disposing the sample within the interior of the tube 16 (i.e., the sample can be carefully slipped inside the tube). Generally speaking, the length of the sample will be equal to or greater than the longitudinal length L of the tube 16, the radial cross-sectional shape of the sample will be the same as the radial cross-sectional shape of the tube, and the diameter of the sample will be roughly the same as the interior diameter D of the tube. As such the sample will completely fill the interior of the tube 16 and the exterior of the tube will be surrounded by air. The sensor 15 is advantageous since the sample can be tested without damaging or disrupting the sample.

Referring again to FIGS. 2-4, the tube 16 is constructed from a material which is non-porous and electrically insulative. By way of example but not limitation, the tube 16 can be constructed from either plastic, or ceramic, or treated paper, or carbon fiber, or the like. The tube 16 provides a means for maintaining the helical structural arrangement and positioning of the helical conductors 17/18/19. The tube 16 also serves as a dielectric between the helical conductors 17/18/

19. In other words, the tube 16 provides a means for preventing the helical conductors 17/18/19 from coming into direct electrical contact with each other. The helical conductors 17/18/19 are constructed from a material which is electrically conductive. By way of example but not limitation, the helical conductors can be constructed from a variety of different metals such as copper, brass, nickel alloy, stainless steel, gold, platinum, silver, and the like.

In the helical sensor embodiment exemplified in FIGS. 2-4 the tube 16 has a radial cross-sectional shape that is circular. A variety of alternate embodiments of the tube (not shown) are also possible where the tube can have any other radial cross-sectional shape. Thus, the tube can have a radial cross-sectional shape that is oval, triangular, square, rectangular, pentagonal, hexagonal or octagonal, among others.

In the helical sensor embodiment exemplified in FIGS. 2-4 the helical conductors 17/18/19 have a radial cross-sectional shape that is rectangular and are located in grooves on the exterior surface of the tube 16 such that the helical conductors are flush with the exterior surface of the tube. A variety of alternate embodiments of the helical conductors (not shown) are also possible. By way of example but not limitation, rather than having a radial cross-sectional shape that is rectangular the helical conductors can also have any other radial cross-sectional shape. Thus, the helical conductors can have a radial cross-sectional shape that is flat, circular, oval, square, pentagonal, hexagonal or octagonal, among others. Furthermore, rather than being located in grooves on the exterior surface of the tube the helical conductors can also be located in grooves on the interior surface of the tube such that the helical conductors are flush with the interior surface of the tube. The helical conductors can also be embedded within the wall of the tube such that the helical conductors are located between the interior surface and exterior surface of the tube. The helical conductors can also be deposited onto the exterior surface of the tube using either a rotary silk screening procedure, or a liquid deposition procedure, or a vapor deposition procedure. The helical conductors can also be deposited onto the interior surface of the tube using either a rotary silk screening procedure, or a liquid deposition procedure, or a vapor deposition procedure. The helical conductors can also be formed on the exterior surface of the tube using an etching procedure. The helical conductors can also be formed on the interior surface of the tube using an etching procedure.

As described heretofore, in the helical sensor embodiment exemplified in FIGS. 2-4 the proximal end 13 of the tube 16 and the distal end 14 of the tube are open. An alternate embodiment (not shown) of the sensor 15 is also possible where a first cap seals the proximal end of the tube and a second cap seals the distal end of the tube such that the interior of the tube is always filled with air. The first and second caps are constructed from a material which is nonporous and electrically insulative. The first and second caps can either be constructed from the same material that the tube is constructed from, or the first and second caps can be constructed from a different material than that which the tube is constructed from. This embodiment of the sensor can be used to test a composite medium 12 in situ by disposing the sensor in the medium such that the exterior surface of the tube is surrounded by the medium. Additionally, a plurality of sensors can be stacked one on top of another resulting in a "macro-sensor" which can be used to test the medium at different depths. By way of example but not limitation, if four different sensors each having a longitudinal length of six inches are stacked one on top of another to form a macro-sensor which is longitudinally inserted into the medium, the medium could be independently tested at a depth of six inches, 12 inches, 18 inches and 24 inches.

Referring again to FIGS. 2-4, the aforementioned longitudinal length L of the tube 16, interior diameter D of the tube, wall thickness T of the tube and conductor winding angle A can have a variety of different sizes. Generally speaking, the size of the length L, diameter D, wall thickness T and winding angle A all relate to the helical length of the helical conductors 17/18/19 and the transmission lines which are formed therefrom. The longer the helical length of the helical conductors the higher the precision of the measurements produced by the helical sensor 15. The helical sensor embodiments described herein are advantageous since a sensor having a small length L and diameter D produces helical conductors having a large helical length. By way of example but not limitation, a sensor having three helical conductors, a length L of 4 inches, a diameter D of 2.25 inches, a wall thickness T of 1/16 of an inch, and a winding angle A of 10 degrees produces a helical length for each helical conductor of almost 39 inches. This relatively small length L and diameter D of the sensor are advantageous for a variety of different reasons, including but not limited to the fact that the sensor can be more easily disposed in the medium being tested.

Referring again to FIGS. 2-4, the size of the longitudinal length L of the tube 16, interior diameter D of the tube, wall thickness T of the tube and conductor winding angle A for a given helical sensor 15 can be tailored to factors such as the particular type of medium being tested 12, the particular dielectric influences in the medium and/or characteristics of the medium which are being measured, and the particular manner in which the testing is performed (e.g., whether the medium is being tested in situ or a sample of the medium is being tested in a different setting such as a laboratory environment or the like). By way of example but not limitation, in the situation where a sample of a medium such as soil is being tested in a laboratory environment, the sensor employs three helical conductors, each helical conductor is flat, each helical conductor has a thickness of 4/1000 of an inch and a width of 20/1000 of an inch, and the tube has a radial cross-sectional shape that is circular, the sensor may have a diameter D of 1/8 of an inch, a length L of 1.5 inches, a wall thickness T of 20/1000 of an inch and a winding angle A of 14 degrees, resulting in each helical conductor having a helical length of 4.7 inches. Such a "miniaturized" version of the sensor is advantageous since it can be used to make measurements at different locations in the sample without significantly disturbing the sample. Such a miniaturized sensor is further advantageous for in situ applications where the sensor needs to be placed in very small spaces.

Referring again to FIGS. 2-4, it is noted that the following considerations exist when selecting the particular size of the conductor winding angle A that is used for the helical sensor 15. Reducing the winding angle A increases the helical length of the helical conductors 17/18/19 which as described heretofore will generally increase the precision of the measurements produced by the sensor. However, if the winding angle A becomes too small the spacing between adjoining turns of the helical conductors can be reduced to the point where the probability of a short occurring between adjoining turns of the helical conductors starts to increase, thus reducing the reliability of the sensor. Practically speaking, for a given helical sensor embodiment the size of the winding angle A is selected to maximize the helical length of the helical conductors without compromising the reliability of the sensor to any significant degree.

Referring again to FIGS. 2-4, in an exemplary embodiment of the helical sensor 15 and related TDR electronics 11 described herein a first original electrical pulse can be transmitted into the proximal end 13 of the first helical conductor 17 such that the first conductor provides a helical conductive means for propagating the first original pulse from the proximal end of the sensor toward the distal end 14 of the sensor, and for propagating a resulting first reflected electrical pulse from the distal end of the sensor back toward the proximal end of the sensor. A second original electrical pulse can be transmitted into the proximal end of the third helical conductor 19 such that the third conductor provides a helical conductive means for propagating the second original pulse from the proximal end of the sensor toward the distal end of the sensor, and for propagating a resulting second reflected electrical pulse from the distal end of the sensor back toward the proximal end of the sensor. The second helical conductor 18 can serve as a helical conductive means for providing an electrical return path for the first and second original pulses, and for the first and second reflected pulses. In other words, the first helical conductor and the second helical conductor form a first "balanced" two-wire transmission line, and the third helical conductor and the second helical conductor form a second balanced two-wire transmission line.

Referring again to FIGS. 2-4, the first original electrical pulse transmitted into the first helical conductor 17 generates a first electromagnetic (EM) energy wave which propagates along the first transmission line toward the distal end 14 of the helical sensor 15 in conjunction with this first original pulse as described heretofore. The second original electrical pulse transmitted into the third helical conductor 19 generates a second EM energy wave which propagates along the second transmission line toward the distal end of the sensor in conjunction with this second original pulse. The first reflected electrical pulse on the first transmission line generates a third EM energy wave which propagates along the first transmission line back toward the proximal end 13 of the sensor in conjunction with this first reflected pulse as described heretofore. The second reflected pulse on the second transmission line generates a fourth EM energy wave which propagates along the second transmission line back toward the proximal end of the sensor in conjunction with this second reflected pulse. The first and third EM energy waves have both an electric field component and a magnetic field component which propagate between the first and second helical conductors 17 and 18. Similarly, the second and fourth EM energy waves have both an electric field component and a magnetic field component which propagate between the third and second helical conductors 19 and 18.

As is appreciated in the art of electromagnetism, the relative permittivity (also known as the dielectric constant) of a material specifies a measure of the material's ability to transmit (i.e., "permit") an electric field. For example, the relative permittivity of air at room temperature (e.g., 70 degrees F.) is approximately one. The relative permittivity of water at room temperature is approximately 80. Generally speaking and referring again to FIGS. 2-4, the relative permittivity of the medium being tested changes in conjunction with changes in the amount of liquid which is present within the medium. More particularly, as the liquid content of the medium increases the relative permittivity of the medium increases. Correspondingly, as the liquid content of the medium decreases the relative permittivity of the medium decreases. These changes in the relative permittivity of the medium affect the original and reflected electrical pulses as follows.

As is appreciated in the art of TDR, as the liquid content of the medium increases the velocity of the first and second original electrical pulses as they propagate along the first and second transmission lines toward the distal end of the sensor decreases, and the velocity of the first and second reflected electrical pulses as they propagate along the first and second transmission lines back toward the proximal end of the sensor similarly decreases. Correspondingly, as the liquid content of the medium decreases the velocity of the first and second original pulses as they propagate along the first and second transmission lines toward the distal end of the sensor increases, and the velocity of the first and second reflected pulses as they propagate along the first and second transmission lines back toward the proximal end of the sensor similarly increases. The elapsed time between when the first original pulse is transmitted into the proximal end of the sensor and when the first reflected pulse is received at the proximal end of the sensor is referred to hereafter as a first "pulse phase delay." Similarly, the elapsed time between when the second original pulse is transmitted into the proximal end of the sensor and when the second reflected pulse is received at the proximal end of the sensor is referred to hereafter as a second pulse phase delay. In one embodiment of the system environment described heretofore the aforementioned signal processor module can determine the current volumetric liquid content of the medium being tested by computing the first and second pulse phase delays, where the liquid content is inferred from the size of these delays.

Generally speaking and as is appreciated in the arts of hydrology and soil science, any salt which is present in the medium being tested will naturally be absorbed into a liquid which is present in the medium. As the salinity of the liquid within the medium increases, the impedance of the helical sensor generally decreases. Although the aforementioned first and second pulse phase delays are little affected by this impedance decrease, the impedance decrease attenuates the amplitude of the first and second reflected pulses which are received at the proximal end of the helical sensor embodiments described herein. The difference between the amplitude of the first original electrical pulse which is transmitted into the proximal end of the sensor and the amplitude of the first reflected electrical pulse which is received at the proximal end of the sensor is referred to hereafter as a first "pulse amplitude difference." Similarly, the difference between the amplitude of the second original electrical pulse which is transmitted into the proximal end of the sensor and the amplitude of the second reflected electrical pulse which is received at the proximal end of the sensor is referred to hereafter as a second pulse amplitude difference. In another embodiment of the system environment, the signal processor module can determine the current salinity of the medium being tested by computing the first and second pulse amplitude differences, where the salinity of the medium is inferred from the size of these differences.

When the medium under test is highly dissipative (such as a medium having a liquid present therein and a high salinity), the amplitude of the reflected electrical pulses can be attenuated and noise can be introduced into the reflected pulses to a degree which can hamper the precision of the measurements being made in the medium. Additional embodiments of the helical sensor described herein are possible where a dielectric coating having a prescribed thickness is applied to the sensor as follows, where the dielectric coating provides a means for allowing the sensor to make precise measurements when the medium is highly dissipative. In the sensor embodiments described heretofore where the proximal end of the tube and the distal end of the tube are open and the helical conductors are either located in grooves on the interior surface of the tube, or are deposited onto the interior surface of the tube using either a rotary silk screening procedure, or a liquid deposition procedure, or a vapor deposition procedure, or are formed on the interior surface of the tube using an etching procedure, the dielectric coating is applied to the interior surface of the tube on top of the helical conductors. The dielectric coating thus serves as a non-conducting insulator between the helical conductors and the medium under test which is disposed within the interior of the tube as described heretofore. In the sensor embodiments described heretofore where the proximal end of the tube and the distal end of the tube are each sealed with a cap and the helical conductors are either located in grooves on the exterior surface of the tube, or are deposited onto the exterior surface of the tube using either a rotary silk screening procedure, or a liquid deposition procedure, or a vapor deposition procedure, or are formed on the exterior surface of the tube using an etching procedure, the dielectric coating is applied to the exterior surface of the tube on top of the helical conductors. The dielectric coating thus serves as a non-conducting insulator between the helical conductors and the medium under test which surrounds the exterior surface of the tube as described heretofore.

Exemplary materials which can be used for the dielectric coating include, but are not limited to, plastic, epoxy, enamel, and the like. It is noted that the following considerations exist when selecting the particular thickness of the dielectric coating that is used. Increasing the thickness of the dielectric coating will reduce the attenuation of the amplitude of the reflected pulses and reduce the noise introduced into the reflected pulses, which will generally enhance the precision of the measurements being made in a medium having a high salinity. However, increasing the thickness of the dielectric coating will also reduce the pulse phase delays, which can degrade the precision of the measurements. In an exemplary embodiment of the helical sensor described herein a thickness of $10/1000$ of an inch is employed for the dielectric coating, which provides a practical balance of these considerations.

When the impedance of the medium under test is close to or the same as the impedance of the aforementioned transmission lines, the amplitude of the reflected electrical pulses can also be attenuated to a degree which can hamper the precision of the measurements being made in the medium. Additional embodiments of the helical sensor described herein are possible where each helical conductor has a linear return path which will now be described. The linear return path for each helical conductor provides a means for allowing the sensor to make precise measurements of the medium regardless of the impedance of the medium. It is noted that the return path of each helical conductor remains un-terminated.

In the sensor embodiments described heretofore where the proximal end of the tube and the distal end of the tube are open and the helical conductors are either located in grooves on the interior surface of the tube, or are deposited onto the interior surface of the tube using either a rotary silk screening procedure, or a liquid deposition procedure, or a vapor deposition procedure, or are formed on the interior surface of the tube using an etching procedure, or are embedded within the wall of the tube, the linear return path for each helical conductor is formed as follows. The helical conductor is folded radially outward along the distal end of the tube and then folded longitudinally upward along the exterior surface of the tube such that the helical conductor runs in a longitudinally linear manner along the exterior surface of the tube back to the proximal end of the tube. Since the exterior of the tube will be surrounded by air as described heretofore, the return path of each helical conductor is surrounded by air. This insures that the reflected electrical pulses will have an amplitude that is large enough for good precision measurements to be made in the medium regardless of the impedance of the medium.

Figure 5:
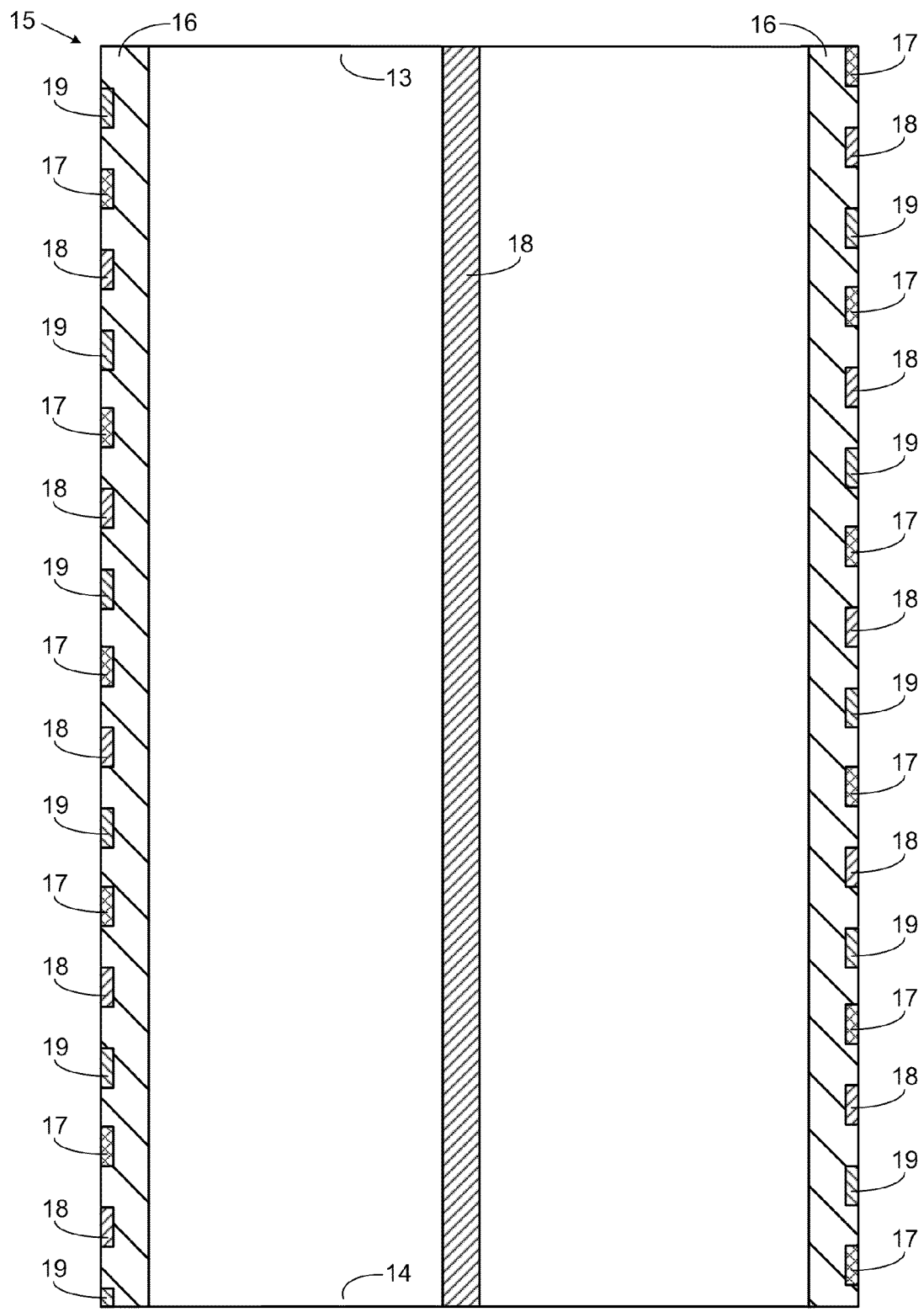
FIG. 5 is a diagram illustrating a longitudinal cross-sectional view, in simplified form, of an alternate embodiment of the helical sensor where each of the sensor's helical conductors has a linear return path.

In the sensor embodiments described heretofore where the proximal end of the tube and the distal end of the tube are each sealed with a cap and the helical conductors are either located in grooves on the exterior surface of the tube, or are deposited onto the exterior surface of the tube using either a rotary silk screening procedure, or a liquid deposition procedure, or a vapor deposition procedure, or are formed on the exterior surface of the tube using an etching procedure, or are embedded within the wall of the tube, the linear return path for each helical conductor is formed as follows. The helical conductor is folded radially inward along the distal end of the tube and then folded longitudinally upward along the interior surface of the tube such that the helical conductor runs in a longitudinally linear manner along the interior surface of the tube back to the proximal end of the tube. FIG. 5 illustrates an exemplary embodiment of a return path for one of the helical conductors. More particularly, FIG. 5 illustrates a longitudinal cross-sectional view, in simplified form, of a linear return path for the aforementioned second helical conductor 18. Since the interior of the tube is always filled with air as described heretofore, the return path of each helical conductor is surrounded by air. This insures that the reflected electrical pulses will have an amplitude that is large enough for good precision measurements to be made in the medium regardless of the impedance of the medium.

1.3 Inner-Conducting Helical Sensor

In the helical sensor embodiments described herein where the proximal end of the tube and the distal end of the tube are open and the helical conductors are either located in grooves on the interior surface of the tube, or are deposited onto the interior surface of the tube using a rotary silk screening procedure, or are formed on the interior surface of the tube using an etching procedure, the sensor can in one implementation also include an inner conductor which runs along the longitudinal axis of the tube from the proximal end of the tube to the distal end of the tube. A variety of embodiments of the inner conductor are possible. By way of example but not limitation, the inner conductor can be linear, can have an axial interior that is either solid or hollow, and can have a variety of radial cross-sectional shapes such as those which are described heretofore for the tube. Additionally, rather than being linear, the inner conductor can also be helical. A bore is formed along the longitudinal axis of the sample of the composite medium which is being tested. The bore has a radial cross-sectional shape which is the same as the radial cross-sectional shape of the inner conductor, and the bore has an interior diameter which is roughly the same as the diameter of the inner conductor. The inner conductor is disposed within the bore so that the inner conductor completely fills the bore.

The distal end of the inner conductor is un-terminated. The inner conductor can either have a longitudinal length which is the same as the length L of the tube, or which is greater than the length L of the tube. The inner conductor is constructed from a material which is electrically conductive, such as any of the materials that are described herein for the helical conductors. The inner conductor can also be constructed by sintering a powdered form of any of these electrically conductive materials. The inner conductor can also be formed as a composite material using vapor deposition, liquid deposition, or flame deposition of any of these electrically conductive materials on top of a non-conductive material. The inner conductor can either be constructed from the same material as the helical conductors, or it can be constructed from a different electrically conductive material. The inner conductor forms a different coaxial transmission line with each of the helical conductors, where these coaxial transmission lines have a common length and each coaxial transmission line runs from the proximal end of the inner-conducting helical sensor to the distal end thereof.

1.4 Open Sensor for Testing a Split Sample of a Composite Medium

This section describes additional embodiments of the helical sensor which are generally applicable to testing a split (i.e., longitudinally halved) sample of a composite medium. These embodiments are referred to hereafter as an "open sensor" embodiments. It is noted that these embodiments inter-operate with the aforementioned TDR electronics in a variety of manners which are similar to those which are described herein for the helical sensor.

Figure 6:
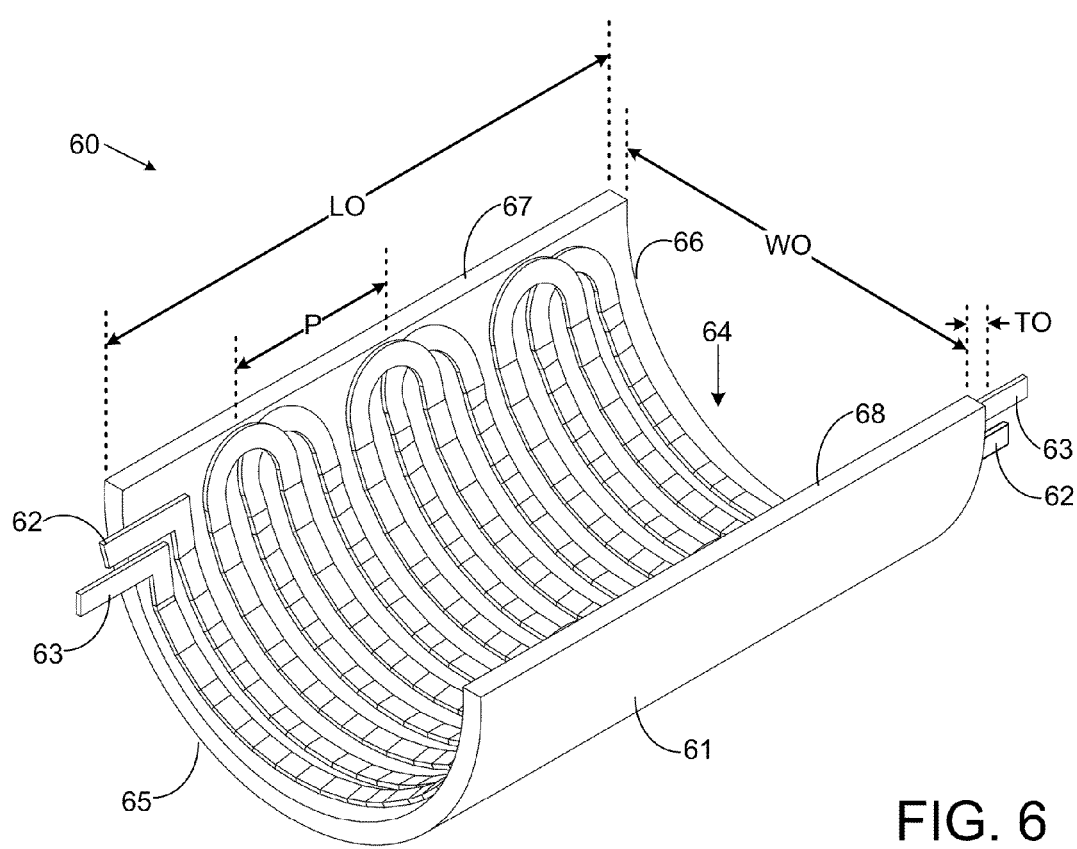
FIG. 6 is a diagram illustrating a side perspective view, in simplified form, of an exemplary embodiment of an open sensor for testing a split sample of a composite medium.

FIG. 6 illustrates a side perspective view, in simplified form, of an exemplary embodiment of an open sensor for testing a split sample of a composite medium. As exemplified in FIG. 6, the open sensor 60 generally includes a longitudinal section of a tube 61 and a plurality of serpentine conductors 62 and 63 which are successively layered on top of each other. It is noted that although the open sensor embodiment exemplified in FIG. 6 includes just two serpentine conductors 62 and 63, alternate embodiments of the open sensor (not shown) are also possible where the sensor includes a number of serpentine conductors which is greater than two. The interior surface of the tube section 61 forms a trough 64 into which the split sample of the composite medium (not shown) is disposed.

Referring again to FIG. 6, one or more serpentine conductors 62 each have a dielectric coating (not shown) applied to their upper surface. The dielectric coating has a prescribed thickness and serves as a non-conducting insulator between the plurality of serpentine conductors 62 and 63. Exemplary materials which can be used for the dielectric coating include, but are not limited to, any of the materials which have been described heretofore for the dielectric coating on the helical sensor. The bottommost serpentine conductor 62 runs along the interior surface of the tube section 61. The topmost serpentine conductor 63 is layered on top of the one or more serpentine conductors. Each serpentine conductor 62 and 63 runs from the proximal end 65 of the tube section 61 to the distal end 66 of the tube section in a repeating serpentine pattern which extends from a first longitudinal side 67 of the interior surface of the tube section to a second longitudinal side 68 of this interior surface. The repeating serpentine pattern has a prescribed longitudinal period P.

Referring again to FIG. 6, the plurality of serpentine conductors 62 and 63 are longitudinally offset from each other such that the conductors are interleaved along the interior surface of the tube section 61, and the conductors cross each other only at the first and second longitudinal sides 67 and 68 of the interior surface of the tube section 61. The plurality of serpentine conductors 62 and 63 are equally spaced from each other and have a common length. The distal end of each serpentine conductor 62 and 63 is un-terminated.

Referring again to FIG. 6, the tube section 61 has a prescribed longitudinal length LO, a prescribed trough width WO and a prescribed wall thickness TO. The length LO, width WO, thickness TO and longitudinal period P can have a variety of different sizes. Generally speaking, the size of the length LO, width WO, thickness TO and period P all relate to the length of the serpentine conductors 62 and 63 and the transmission lines which are formed therefrom. The longer the length of the serpentine conductors the higher the precision of the measurements produced by the open sensor 60.

The open sensor embodiments described herein are advantageous since a sensor having a small length LO and width WO produces serpentine conductors having a large length. The size of the length LO, width WO and thickness TO for a given open sensor can be tailored to factors such as the particular type of medium being tested, and the particular dielectric influences in the medium and/or characteristics of the medium which are being measured. Generally speaking, the length of the split sample will be equal to or greater than the longitudinal length LO of the tube section 61, the radial cross-sectional shape of the split sample will be the same as the radial cross-sectional shape of the tube section, and the width of the split sample will be roughly the same as the trough width WO. As such, the split sample will completely fill the trough 64 and the exterior of the tube section 61 will be surrounded by air. The open sensor 60 is advantageous since the split sample can be tested without damaging or disrupting the sample.

Referring again to FIG. 6, it is noted that the following considerations exist when selecting the particular size of the longitudinal period P that is used for the open sensor 60. Reducing the period P increases the length of the serpentine conductors 62 and 63 which as described heretofore will generally increase the precision of the measurements produced by the sensor. However, if the period P becomes too small the spacing between adjoining runs of the serpentine conductors can be reduced to the point where the probability of a short occurring between adjoining runs of the serpentine conductors starts to increase, thus reducing the reliability of the sensor. Practically speaking, for a given open sensor embodiment the size of the period P is selected to maximize the length of the serpentine conductors without compromising the reliability of the sensor to any significant degree.

Referring again to FIG. 6, the tube section 61 is constructed from a material which is non-porous and electrically insulative, such as any of the exemplary materials which have been described heretofore for the tube of the helical sensor. The tube section provides a means for maintaining the structural arrangement and positioning of the serpentine conductors 62 and 63, and also serves as a dielectric between the conductors. In the open sensor embodiment exemplified in FIG. 6 the tube section has a radial cross-sectional shape that is semi-circular. A variety of alternate embodiments of the tube section (not shown) are also possible where the tube section can have any other radial cross-sectional shape, such as a section of any of the radial cross-sectional shapes which have been described heretofore for the tube of the helical sensor.

Referring again to FIG. 6, the serpentine conductors 62 and 63 are constructed from any material which is electrically conductive, such as any of the exemplary materials which have been described heretofore for the helical conductors of the helical sensor. In the open sensor embodiment exemplified in FIG. 6 the serpentine conductors have a radial cross-sectional shape that is rectangular. A variety of alternate embodiments of the serpentine conductors (not shown) are also possible where the serpentine conductors can have any other radial cross-sectional shape, such as any of the radial cross-sectional shapes which have been described heretofore for the helical conductors of the helical sensor. The serpentine conductors can also be deposited onto the interior surface of the tube section 61 using either a rotary silk screening procedure, or a liquid deposition procedure, or a vapor deposition procedure. The serpentine conductors can also be formed on the interior surface of the tube section using an etching procedure.

Referring again to FIG. 6, a variety of additional embodiments of the open sensor 60 described herein are possible. In one alternate embodiment of the open sensor a topmost dielectric coating (not shown) having a prescribed thickness can be applied to the interior surface of the tube section 61 on top of the topmost serpentine conductor 63 which is layered on top of the one or more serpentine conductors 62. The topmost dielectric coating serves as a non-conducting insulator between the plurality of serpentine conductors and the split sample of the medium being tested. Thus, the topmost dielectric coating provides a means for allowing the sensor to make precise measurements when the split sample of the medium is highly dissipative. Exemplary materials which can be used for the topmost dielectric coating include, but are not limited to, any of the materials which have been described heretofore for the dielectric coating on the helical sensor. The considerations that exist when selecting the particular thickness of the topmost dielectric coating are similar to those which have been described heretofore for the dielectric coating on the helical sensor.

In another alternate embodiment of the open sensor each serpentine conductor can have a linear return path which provides a means for allowing the sensor to make precise measurements of the split sample of the medium regardless of the impedance of the medium. It is noted that the return path of each serpentine conductor remains un-terminated and is formed in a manner which is similar to that which has been described heretofore for the return paths on the helical sensor.

In yet another alternate embodiment of the open sensor the sensor can include a conductive element which is disposed on top of the split sample of the medium after the sample has been disposed into the trough of the tube section, where the conductive element runs along the longitudinal center of the top of the sample from the proximal end of the sample to the distal end of the sample. A variety of embodiments of the conductive element are possible. By way of example but not limitation, the conductive element can have an axial interior that is either solid or hollow, and can have a variety of radial cross-sectional shapes such as those which are described heretofore for the for the helical conductors of the helical sensor. The distal end of the conductive element is un-terminated. The conductive element can either have a length which is the same as the length of the tube section, or which is greater than the length of the tube section. The conductive element is constructed from any material which is electrically conductive, such as any of the materials that are described herein for the helical conductors of the helical sensor. The conductive element can also be constructed/formed in any of the ways which have been described heretofore for the inner conductor of the inner-conducting helical sensor. The conductive element can either be constructed from the same material as the serpentine conductors, or it can be constructed from a different material. The conductive element forms a different "semi-coaxial" transmission line with each of the serpentine conductors, where these semi-coaxial transmission lines have a common length and each semi-coaxial transmission line runs from the proximal end of the tube section to the distal end thereof.

2.0 Additional Embodiments

While the helical sensor and open sensor have been described in more detail by specific reference to embodiments thereof, it is understood that variations and modifications thereof can be made without departing from the true spirit and scope of the helical and open sensors. By way of example but not limitation, alternate embodiments of the helical sensor are possible where the sensor includes a number of helical conductors which is greater than three. Additionally, rather than implementing the helical and open sensor embodiments described herein in a system environment which employs TDR electronics that include a signal processor module which analyzes the reflected pulse it receives from each transmission line in the time-domain as described heretofore, alternate embodiments of the helical sensor and open sensor are possible where the system environment employs a different type of electronics that include a signal processor module which analyzes the reflected pulse it receives from each transmission line in the frequency-domain.

Alternate embodiments of the helical sensor are also possible where the tube is constructed from an inflatable elastic material which is non-porous and electrically insulative, such as rubber and the like. In the case where the proximal end of the tube and the distal end of the tube are open and the sensor is used to test a sample of a composite medium by disposing the sample within the interior of the tube as described heretofore, once the sample is slipped inside the tube the tube can be inflated in order to firmly press the tube and the helical conductors which are wound there-around against the outer surface of the sample. In the case where the proximal end of the tube and the distal end of the tube are each sealed with a cap such that the interior of the tube is always filled with air, and the sensor is used to test the medium in situ as described heretofore, once the sensor is disposed in the medium the tube can be inflated in order to firmly press the tube and the helical conductors against the medium. These alternate embodiments ensure that the sensor has good contact with the medium being tested along the entire surface of the sensor. Thus, these alternate embodiments can optimize the accuracy of the testing.

Alternate embodiments of the helical sensor and related TDR electronics are also possible where an original electrical pulse is transmitted into the proximal end of the second helical conductor such that the second conductor provides a helical conductive means for propagating the original pulse from the proximal end of the sensor toward the distal end of the sensor, and for propagating a resulting reflected electrical pulse from the distal end of the sensor back toward the proximal end of the sensor. In this case, the first and third helical conductors can serve as a helical conductive means for providing an electrical return path for the original pulse and for the reflected pulse. In other words, the second helical conductor forms a balanced coaxial transmission line with the first and third helical conductors.

It is also noted that any or all of the aforementioned embodiments can be used in any combination desired to form additional hybrid embodiments. Although the helical sensor embodiments have been described in language specific to structural features and/or methodological acts, it is to be understood that the subject matter defined in the appended claims is not necessarily limited to the specific features or acts described heretofore. Rather, the specific features and acts described heretofore are disclosed as example forms of implementing the claims.

Wherefore, what is claimed is:

1. A helical sensor for testing a composite medium, comprising:
 a tube which is non-porous and electrically insulative; and
 conductors consisting of an odd number thereof greater than one, wherein,
  the conductors are wound in a continuously parallel helix around the tube using a prescribed winding angle such that the conductors are interleaved,
  each turn of each conductor is equally spaced from adjoining turns of the other conductors,
  the conductors comprise a common helical length, and both a proximal end of the tube and a distal end of the tube are open.

2. The helical sensor of claim 1, wherein,
the tube is constructed from either plastic, or ceramic, or treated paper, or carbon fiber, or an inflatable elastic material, and
the tube comprises a radial cross-sectional shape comprising one of a circular shape, or an oval shape, or a triangular shape, or a square shape, or a rectangular shape, or a pentagonal shape, or a hexagonal shape, or an octagonal shape.

3. The helical sensor of claim 1, wherein,
the conductors are constructed from either copper, or brass, or nickel alloy, or stainless steel, or gold, or platinum, or silver, and
the conductors comprise a radial cross-sectional shape comprising one of a rectangular shape, or a flat shape, or a circular shape, or an oval shape, or a square shape, or a pentagonal shape, or a hexagonal shape, or an octagonal shape.

4. The helical sensor of claim 1, wherein either,
the conductors are located in grooves on an exterior surface of the tube such that the conductors are flush with the exterior surface of the tube, or
the conductors are deposited onto the exterior surface of the tube using either a rotary silk screening procedure, or a liquid deposition procedure, or a vapor deposition procedure, or
the conductors are formed on the exterior surface of the tube using an etching procedure.

5. The helical sensor of claim 1, wherein either,
the conductors are located in grooves on an interior surface of the tube such that the conductors are flush with the interior surface of the tube, or
the conductors are deposited onto the interior surface of the tube using either a rotary silk screening procedure, or a liquid deposition procedure, or a vapor deposition procedure, or
the conductors are formed on the interior surface of the tube using an etching procedure.

6. The helical sensor of claim 5, further comprising a dielectric coating which is applied to the interior surface of the tube on top of the conductors.

7. The helical sensor of claim 5, wherein each conductor comprises a linear return path, wherein said return path is formed by folding the conductor radially outward along the distal end of the tube and then folding the conductor longitudinally upward along an exterior surface of the tube such that the conductor runs in a longitudinally linear manner along said exterior surface back to the proximal end of the tube.

8. The helical sensor of claim 5, further comprising an inner conductor which runs along a longitudinal axis of the tube from the proximal end of the tube to the distal end of the tube.

9. The helical sensor of claim 8, wherein the inner conductor is linear and comprises:
a solid axial interior; and
a radial cross-sectional shape comprising one of a circular shape, or an oval shape, or a triangular shape, or a square shape, or a rectangular shape, or a pentagonal shape, or a hexagonal shape, or an octagonal shape.

10. The helical sensor of claim 8, wherein the inner conductor is linear and comprises:
a hollow axial interior; and
a radial cross-sectional shape comprising one of a circular shape, or an oval shape, or a triangular shape, or a square shape, or a rectangular shape, or a pentagonal shape, or a hexagonal shape, or an octagonal shape.

11. The helical sensor of claim 8, wherein the inner conductor is helical.

12. The helical sensor of claim 8, wherein,
the conductors which are wound around the tube are constructed from a material comprising either copper, or brass, or nickel alloy, or stainless steel, or gold, or platinum, or silver, and
the inner conductor is constructed from the same material that the conductors which are wound around the tube are constructed from.

13. The helical sensor of claim 8, wherein,
the conductors which are wound around the tube are constructed from a material comprising either copper, or brass, or nickel alloy, or stainless steel, or gold, or platinum, or silver, and
the inner conductor is constructed from an electrically conductive material that is different than the material that the conductors which are wound around the tube are constructed from.

14. The helical sensor of claim 1, wherein the conductors are embedded within a wall of the tube such that the conductors are located between an interior surface of the tube and an exterior surface of the tube.

15. The helical sensor of claim 1, wherein the size of the winding angle is selected to maximize the helical length of the conductors without compromising the reliability of the helical sensor.

16. The helical sensor of claim 1, wherein the odd number is three.

17. A helical sensor for testing a composite medium, comprising:
a tube which is non-porous and electrically insulative;
a first cap which is non-porous and electrically insulative;
a second cap which is non-porous and electrically insulative; and
three or more conductors which are wound in a continuously parallel helix around the tube using a prescribed winding angle such that the conductors are interleaved, wherein,
the first cap seals a proximal end of the tube and the second cap seals a distal end of the tube such that an interior of the tube is always filled with air,
each turn of each conductor is equally spaced from adjoining turns of the other conductors, and
the conductors comprise a common helical length.

18. The helical sensor of claim 17, wherein either,
the first and second caps are constructed from the same material that the tube is constructed from, or
the first and second caps are constructed from a different material than that which the tube is constructed from.

19. The helical sensor of claim 17, wherein either,
the conductors are located in grooves on an exterior surface of the tube such that the conductors are flush with the exterior surface of the tube, or
the conductors are deposited onto the exterior surface of the tube using either a rotary silk screening procedure, or a liquid deposition procedure, or a vapor deposition procedure, or
the conductors are formed on the exterior surface of the tube using an etching procedure.

20. The helical sensor of claim 19, further comprising a dielectric coating which is applied to the exterior surface of the tube on top of the conductors, wherein said coating has a prescribed thickness.

21. The helical sensor of claim 20, wherein,
the dielectric coating comprises either plastic, or epoxy, or enamel, and
the prescribed thickness is 10/1000 of an inch.

22. The helical sensor of claim 19, wherein each conductor comprises a linear return path, wherein said return path is formed by folding the conductor radially inward along the distal end of the tube and then folding the conductor longitudinally upward along an interior surface of the tube such that the conductor runs in a longitudinal linear manner along said interior surface back to the proximal end of the tube.

23. A helical sensor for testing a composite medium, comprising:
  a first helical conductive means for propagating a first original electrical pulse from a proximal end of the sensor toward a distal end of the sensor, and for propagating a first reflected electrical pulse from the distal end of the sensor back toward the proximal end of the sensor;
  a second helical conductive means for propagating a second original electrical pulse from the proximal end of the sensor toward the distal end of the sensor, and for propagating a second reflected electrical pulse from the distal end of the sensor back toward the proximal end of the sensor;
  a third helical conductive means for providing an electrical return path for the first and second original electrical pulses, and for the first and second reflected electrical pulses, wherein,
    the first, second and third helical conductive means are wound in a continuously parallel helix such that they are interleaved, and
    the first, second and third helical conductive means comprise a common helical length; and
  a non-porous and non-conductive tubular means for maintaining the structural arrangement and positioning of the first, second and third helical conductive means, and for preventing the first, second and third helical conductive means from coming into direct electrical contact with each other.

* * * * *